(12) United States Patent
Neuendorff

(10) Patent No.: US 11,285,097 B2
(45) Date of Patent: Mar. 29, 2022

(54) FRUIT FLAVORINGS PRODUCING A YELLOW TASTE SENSATION

(71) Applicant: Symrise AG, Holzminden (DE)

(72) Inventor: Gabriele Neuendorff, Holzminden (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 16/649,705

(22) PCT Filed: Sep. 26, 2017

(86) PCT No.: PCT/EP2017/074421
§ 371 (c)(1),
(2) Date: Mar. 23, 2020

(87) PCT Pub. No.: WO2019/063067
PCT Pub. Date: Apr. 4, 2019

(65) Prior Publication Data
US 2020/0253857 A1    Aug. 13, 2020

(51) Int. Cl.
| | |
|---|---|
| *A61K 8/92* | (2006.01) |
| *A61K 8/73* | (2006.01) |
| *A61K 8/37* | (2006.01) |
| *A61K 8/31* | (2006.01) |
| *A61K 8/34* | (2006.01) |
| *A61Q 1/06* | (2006.01) |
| *A61Q 11/00* | (2006.01) |
| *A23L 27/12* | (2016.01) |
| *A23G 3/48* | (2006.01) |
| *A23G 4/06* | (2006.01) |

(52) U.S. Cl.
CPC ............... *A61K 8/922* (2013.01); *A23G 3/48* (2013.01); *A23G 4/068* (2013.01); *A23L 27/12* (2016.08); *A61K 8/31* (2013.01); *A61K 8/345* (2013.01); *A61K 8/375* (2013.01); *A61K 8/735* (2013.01); *A61K 8/925* (2013.01); *A61Q 1/06* (2013.01); *A61Q 11/00* (2013.01); *A23V 2002/00* (2013.01)

(58) Field of Classification Search
CPC ........... A23G 3/48; A23G 4/068; A23L 27/12; A61Q 1/06; A61Q 11/00; A61K 8/922; A61K 8/31; A61K 8/345; A61K 8/375; A61K 8/735; A61K 8/925; A23V 2002/00
See application file for complete search history.

(56) References Cited

U.S. PATENT DOCUMENTS

| | | | | |
|---|---|---|---|---|
| 6,695,510 B1 * | 2/2004 | Look | ...................... | A45D 40/04 401/49 |
| 6,723,307 B2 * | 4/2004 | Rose, III | ................. | A61K 8/345 424/401 |
| 2002/0127192 A1 * | 9/2002 | Murphy | ................... | A61K 8/02 424/64 |

FOREIGN PATENT DOCUMENTS

| | | | | |
|---|---|---|---|---|
| CN | 104771351 A | * | 7/2015 | |
| GB | 1337461 A | * | 11/1973 | ............. A61Q 19/00 |

OTHER PUBLICATIONS

Trang. "Fresh Strawberry Melon Juice," Downloaded Sep. 14, 2020 from https://wildwildwhisk.com/fresh-strawberry-melon-juice/ and https://wildwildwhisk.com/wprm_print/recipe/3121. Available online Jul. 28, 2014. (Year: 2014).*
Machine translation of CN 104771351 (A) (Year: 2021).*
Espacenet search Jan. 14, 2021 (Year: 2021).*
Google scholar search Jan. 14, 2021 (Year: 2021).*
Google search Jan. 16, 2021 (Year: 2021).*
Wikipedia Entry for "Pear", downloaded Jan. 16, 2021 from https://en.wikipedia.org/wiki/Pear (Year: 2021).*
Google_search_7-15-21_artificial_strawberry_flavor.pdf (Year: 2021).*
Google_patent_search_7-15-21_lipstick_with_two_flavors_separate_areas.pdf (Year: 2021).*
Google_search_7-15-21_strawberry_kiwi_water_recipe.pdf (Year: 2021).*
G. Brinkley. "Get Great Lips for the New Year," downloaded Jul. 14, 2021 from https://styleonmain.net/get-great-lips-new-year/, available online Jan. 5, 2015. (Year: 2015).*
D. Johnson, ("Strawberry Kiwi infused water recipe," downloaded Jul. 15, 2021 from https://eatingrichly.com/strawberry-kiwi-water-recipe-health-benefits-infused-water/). Available online May 7, 2015 (Year: 2015).*
I. Eduardo, et al. "Identification of key odor volatile compounds in the essential oil of nine peach accessions," J. Sci Food Agric 2010; 90: 1146-1154. (Year: 2010).*
J-P. Rospars, Interactions of Odorants with Olfactory Receptors and Other Preprocessing Mechanisms: How Complex and Difficult to Predict?, Chem. Senses 38: 283-287, 2013. (Year: 2013).*
Somer—Smoothie Chefkoch 1. Mar. 2012 (Mar. 1, 2012) , XP0027811059 Gefunden im Internet: URL: https : //www. chefkoch . de/rezepte/168512 , 1276766586/Somer-Smoothie. html [gefunden am, May 16, 2018.
Smoothie von gefriergetrockneten Kirsche, Banane, Apfel, Heidelbeere in ein Highball-Glas auf weißem Hintergrund. Smoothie von getrockneten Früchten Depositphotos, Sep. 6, 2017.
True fruits Purple, 100% Frucht Beerenmix II , Testberi chte 1., Oct. 1, 2008.
Voel kel Trink Smoothie Bio Kirsch Banane, Testbed chte 1, Oct. 1, 2008.
J . Luehders, "Nice to Meet You! It's Sumertime", May 18, 2017.

* cited by examiner

*Primary Examiner* — Michael P Cohen
(74) *Attorney, Agent, or Firm* — Dilworth & Barrese, LLP

(57) ABSTRACT

The invention relates to a fruit flavoring that produces a yellow taste sensation and that is obtained by (a) contacting and/or mixing at least one fruit flavoring producing a red taste sensation with (b) at least one fruit flavoring producing a green taste sensation.

8 Claims, 1 Drawing Sheet

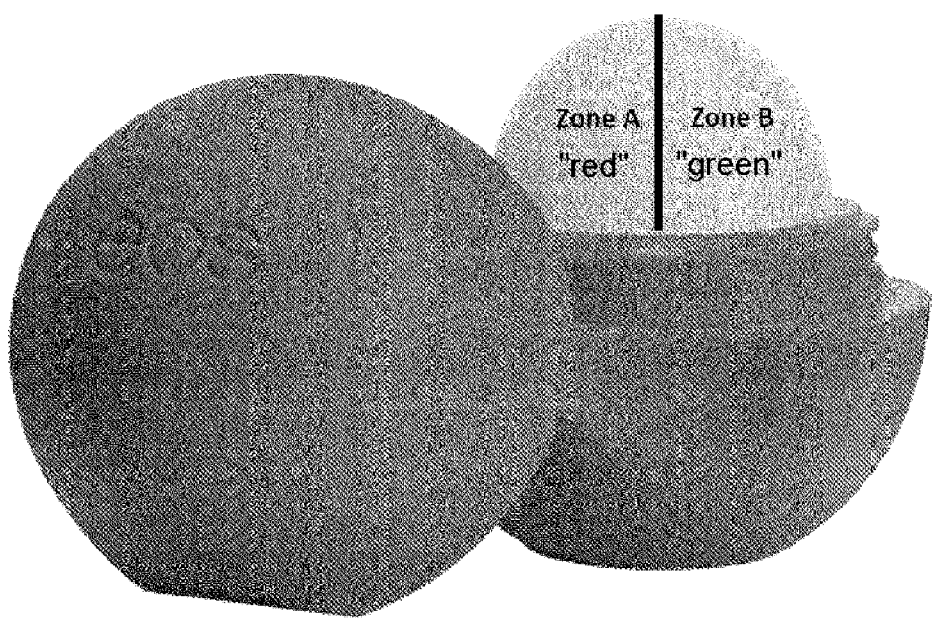

US 11,285,097 B2

FRUIT FLAVORINGS PRODUCING A YELLOW TASTE SENSATION

FIELD OF THE INVENTION

The invention is in the field of decorative cosmetics and relates to fruit flavorings with a yellow taste impression, which can be produced by combining two flavors with a completely different taste impression, various preparations, especially lipsticks, that contain these flavors, and use thereof.

PRIOR ART

Lipstick is among a woman's most important cosmetic articles. However, the history of this indispensable beauty aid did not begin in recent times, but goes back many centuries. The oldest finding that indicates coloring of the lips originates from 3500 B.C. At excavations in the Sumerian city of Ur, researchers discovered a kind of lip salve. It is also often documented that queens such as Nefertiti (about 1350 B.C.) not only painted their lips red, but also accentuated their eyes. Also for men, mainly warriors, colored lips were quite usual.

While it is unclear whether and how women in the Middle Ages used makeup, cosmetics were very popular in the Baroque period. Queen Elizabeth I emphasized her red lips even more by the contrast of her white-powdered face. She is also said to be the first woman to use lip color in stick form.

In 1883, a perfume manufacturer from Paris presented a stick made of colored castor oil, deer tallow and beeswax wrapped in tissue paper at the World Fair in Amsterdam. At first, however, it had a tough time, as it was not only regarded as sinful, but in addition it was also very expensive. The French actress Sarah Bernhardt, a diva of the late 19th century, made lipstick popular, standing on the stage with cherry-red lips. Guerlain was the first to put lipstick in a metal sleeve, in 1910. The triumphant progress of lipstick began conclusively in the Golden Twenties. Starting from 1948, designers encased it in a practical metal sleeve with a sliding mechanism, so that the ladies only colored their lips and not also their fingers or purses. The Revlon brothers Charles and Joseph produced not only the first nail polish, but were also the first to match the color for the nails to that for the lips. The American chemist Hazel Bishop developed the lanolin-based lipstick that does not allow the color to smudge, which is still in use today.

Subsequently, lipstick was able to shake off its "grime" image, and progressed to become the symbol of independence and emancipation. The suffragettes painted their lips bright-red as they marched through New York in 1912. Just for a short time, the mouths of those in Parisian artists' circles were sometimes even a garish green—but after several women died, the toxic verdigris powder was quickly banned again.

In the Second World War, the beautician even gained a patriotic function: the lips of the allied ladies radiated "Victory Red" and "Patriot Red", makeup was regarded as a patriotic duty, which promoted perseverance on the home front. After the English had stopped the production of decorative cosmetics in 1939 in favor of products that were essential to the war effort, the motivation of the female workers fell sharply. They quickly thought better of it and allowed lipsticks to roll off the production line again.

After the lipstick twist-tube was invented in the USA in 1949, the global triumphant progress of the little coloring tube could no longer be halted. Now lipstick has progressed to a high-tech product, which promises more than great durability and flexible application. Cosmetics companies advertise with "networks of hydrating capsules and polymers", "reflecting pigments" or small beads that automatically release a new color by pressing the lips together. The color range has also been expanded. Whereas in the fifties lipsticks could still be bought in red, pink and brown, there are now enticing colors such as "Dance Floor Rouge", "Rum Kiss", "Walk the Catwalk Brown", "Pink in the Limo", "Strawbaby", "Deep Love", "Film Noir".

The selection offered by perfumeries, drugstores, supermarkets and naturally also online of lipsticks of all price ranges seems to meet every desire. Nevertheless, the manufacturers, always looking for something new, need to find an alternative, to satisfy an unmet need, and to set themselves apart from the competition.

The products that are aimed in particular at the interesting target group of girls and women include lipsticks that have a fruit flavor on application, because this is associated with freshness and youthfulness. Also many balms in stick form have fruit flavorings, for example strawberry or apple. There is particular interest in marketing stick products that have two different flavors. This can be achieved by having one half of the stick containing the matrix with one flavor and the other half containing the same matrix but with the other flavor. A different taste is produced, depending on which side of the stick is used.

A challenge that up to now has not yet been overcome is to manufacture sticks that have not two, but three different taste notes, wherein the simplest path—namely simply dividing the stick into three different flavor zones—should not be followed. The present invention is therefore based on the concrete problem of providing preparations, especially cosmetic preparations and primarily stick products, which during use are able to produce three entirely individual flavor notes of the type red, green and yellow, wherein pure mixed notes should be excluded.

DESCRIPTION OF THE INVENTION

The invention relates firstly to A fruit flavoring with a yellow taste impression is proposed, which is obtained by bringing into contact or mixing
(a) at least one fruit flavoring with a red taste impression and
(b) at least one fruit flavoring with a green taste impression.

Surprisingly, it was found that by combining fruit flavorings with a red taste impression ("red flavors") and those with a green taste impression ("green flavors"), fruit flavorings with a yellow taste impression ("yellow flavors") are obtained. They are not mixed flavors, but actually individual flavors, which in each case can be assigned to a specific fruit. For example, by combining strawberry and apple flavor, a definite pear flavor is obtained.

Through spatial separation of the red and the green flavors, for example in different zones of a lipstick, during application the two flavors may either be perceived each individually, or when brought into contact with one another, the yellow taste impression resulting from the red and the green flavor is perceived.

Flavors

In connection with fruit flavorings, the flavor notes yellow, red and green are notoriously familiar to a person skilled in the art, namely a perfumer, so that no further clarification is required per se, as to which taste impressions are connected therewith. However, to exclude any uncertainty, examples of corresponding flavors will be given hereunder:

A yellow taste impression means the flavor that corresponds to or at least comes close to a fruit that is selected from the group that is formed by peach, pear, pineapple, banana or mango.

Red flavors that form group (a) comprise taste impressions of fruits such as for example strawberry, raspberry, blackberry, blueberry and cherry.

Green flavors that form group (b) comprise taste impressions of fruits such as for example kiwi, gooseberry, apple, melon, grape and rhubarb.

The listing of the fruits is to be regarded as illustrative and is not intended to be exhaustive.

In order to produce a yellow flavor, it is recommended to bring into contact or mix the fruit flavorings with a red taste impression and the fruit flavorings with a green taste impression in a weight ratio from about 25:75 to about 75:25. A weight ratio from about 40:60 to about 60:40 is especially preferred, and in particular about 50:50.

Method

The invention further relates to a method for producing a fruit flavoring with a yellow taste impression, comprising or consisting of the following steps:
(i) providing at least one fruit flavoring with a red taste impression (component a),
(ii) providing at least one fruit flavoring with a green taste impression (component b), and
(iii) contacting or mixing the two components (a) and (b).

In a preferred embodiment of the present invention, the contacting of the two components (a) and (b) takes place on the human skin or mucosa. This is to be understood as meaning that the components (a) and (b) are indeed applied on the lips jointly, but separately from one another, for example in the form of a lipstick with different flavor zones, and the mixing takes place at the site of application. It is also possible to encapsulate the flavors and then for example add them to a fruit gum, so that during consumption a constant succession of different taste impressions is created.

Encapsulation

The red and the green flavors may be incorporated in identical or different matrixes (called carriers here). It is, however, also possible, depending on the field of use, to encapsulate at least one of the two components, so that the corresponding taste impression is delayed, for example when incorporated in a toothpaste.

Capsules that contain one or more flavorings are to be understood as spherical aggregates, which contain at least one solid or liquid core, which is surrounded by at least one continuous shell. The flavorings may be encapsulated by coating materials and then be in the form of macrocapsules with diameters from about 0.1 to about 5 mm or microcapsules with diameters from about 0.0001 to about 0.1 mm.

Coating Materials

Suitable coating materials are for example starches, including their degradation products and derivatives produced chemically or physically (especially dextrins and maltodextrins), gelatin, gum arabic, agar, ghatti gum, gellan gum, modified and unmodified celluloses, pullulan, curdlan, carrageenans, alginic acid, alginates, pectin, inulin, xanthan gum and mixtures of two or more of these substances.

The solid encapsulation material is preferably a gelatin (especially porcine, bovine, poultry and/or fish gelatin), wherein these preferably have a swelling factor greater than or equal to 20, preferably greater than or equal to 24. Among these substances, gelatin is especially preferred, as it is readily available and can be purchased with different swelling factors.

Maltodextrins are also preferred (in particular based on cereals, especially maize, wheat, tapioca or potatoes), which preferably have DE values in the range from 10 to 20. Others that are preferred are celluloses (e.g. cellulose ether), alginates (e.g. sodium alginate), carrageenan (e.g. beta-, iota-, lambda- and/or kappa-carrageenan), gum arabic, curdlan and/or agar.

Alginate capsules are also preferred, as described in detail for example in the following documents: EP 0389700 A1, U.S. Pat. Nos. 4,251,195, 6,214,376, WO 2003 055587 or WO 2004 050069 A1.

In a further preferred embodiment, the shell of the capsules consists of melamine-formaldehyde resins or coacervation products from cationic monomers or biopolymers (e.g. chitosan) and anionic monomers, such as for example (meth)acrylates or alginates.

Encapsulation Method

The capsules are generally finely dispersed liquid or solid phases enveloped in film-forming polymers, in the production of which the polymers, after emulsification and coacervation or interfacial polymerization, are precipitated on the enveloping material. According to another method, molten waxes are taken up in a matrix ("microsponge"), which may as microparticles additionally be enveloped in film-forming polymers. According to a third method, particles are coated alternately with polyelectrolytes of different charge ("layer-by-layer" method). The microscopically small capsules may be dried as powder. Besides single-core microcapsules, multicore aggregates, also called microspheres, are also known, which contain two or more cores distributed in the continuous shell material. Single-core or multicore microcapsules may also be enclosed in an additional second, third etc. shell. The shell may consist of natural, semisynthetic or synthetic materials. Natural shell materials are for example gum arabic, agar, agarose, maltodextrins, alginic acid or salts thereof, e.g. sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic shell materials are, among others, chemically modified celluloses, especially cellulose esters and ethers, e.g. cellulose acetate, ethylcellulose, hydroxypropylcellulose, hydroxypropylmethylcellulose and carboxymethylcellulose, and starch derivatives, especially starch ethers and esters. Synthetic shell materials are for example polymers such as polyacrylates, polyamides, polyvinyl alcohol or polyvinylpyrrolidone.

Examples of microcapsules of the prior art are the following commercial products (in each case the shell material is given in parentheses): Hallcrest Microcapsules (gelatin, gum arabic), Coletica Thalaspheres (marine collagen), Lipotec Millicapseln (alginic acid, agar), Induchem Unispheres (lactose, microcrystalline cellulose, hydroxypropylmethylcellulose); Unicerin C30 (lactose, microcrystalline cellulose, hydroxypropylmethylcellulose), Kobo Glycospheres (modified starch, fatty acid esters, phospholipids), Softspheres (modified agar) and Kuhs Probiol Nanospheres (phospholipids) as well as Primaspheres and Primasponges (chitosan, alginates) and Primasys (phospholipids).

Chitosan microcapsules and methods of production thereof are adequately known from the prior art [WO 01/01926, WO 01/01927, WO 01/01928, WO 01/01929]. Microcapsules with average diameters in the range from 0.0001 to 5, preferably 0.001 to 0.5 and especially 0.005 to 0.1 mm, consisting of a shell membrane and a matrix containing the active substances, may be obtained for example by (a) preparing a matrix from gelling agents, cationic polymers and active substances,
(b) optionally dispersing the matrix in an oily phase,
(c) treating the dispersed matrix with aqueous solutions of anionic polymers, optionally removing the oily phase.

Steps (a) and (c) are interchangeable, by using anionic polymers instead of the cationic polymers in step (a), and vice versa.

The capsules may also be produced by enveloping the active substance alternately with layers of differently charged polyelectrolytes (layer-by-layer technology). In this connection, reference may be made to European Patent EP 1064088 B1 (Max-Planck company).

Cosmetic Preparations

The invention further relates to cosmetic preparations containing (a) a carrier with at least one fruit flavoring with a red taste impression and
(b) a carrier with at least one fruit flavoring with a green taste impression, wherein the two carriers (a) and (b) are spatially separated from one another, but are adjacent.

Although it is of course basically possible to incorporate the two components in any cosmetic preparation, effecting spatial separation, for example by encapsulating at least one of the two components, so that release of the encapsulated flavorings is delayed at first, with release by mechanical stressing (e.g. by rubbing in), this variant is not preferred.

The actual sense of the invention is, as described at the beginning, that a taste sensation but no odor sensation is triggered, in which two discrete flavors in the mixture produce a further individual note. For this it is necessary for the flavors to be directed to the taste buds, because only then can a corresponding impression be produced in the brain.

The preferred form of cosmetic use is therefore in the field of decorative cosmetics, in particular a lipstick. These are to be understood both as products intended to color the lips, and those exclusively for personal care ("lip balm sticks"). As the name lipstick already indicates, the corresponding products are in the form of a stick, which is usually bevelled at the tip, to facilitate application.

For production, the liquid lipstick mass is poured into previously greased aluminum molds, cooled extremely quickly and then projected by air pressure backwards out of the mold and into the rotating or spring mechanism. After the stick has been turned round, it is briefly flamed, so that the feed point is smoothed, and the stick acquires more gloss. Even more gloss and surface shine are provided by a fine spray mist of silicone.

By means of the rotating or spring mechanism, the stick is moved out of the container, so that always only the part that is required for application projects from the case. Alternatively, however, the lipsticks in the sense of the present invention may also have other shapes. In particular, they may be sticks with the profile of a hemisphere, such as those marketed for example under the names "EOS" or "LABELINO". As already explained at the beginning, the most intense taste experience is achieved if the two flavors red and green are mixed in roughly equal amounts. When used as lipstick, however, no mixtures are produced, instead the two taste zones are brought into contact on the surface of the lips. Correspondingly, in that case the best effect is achieved if the two flavor areas are roughly equal in size, as is also illustrated in the FIGURE. Division of the areas then takes place, for obvious reasons, horizontally and not vertically, because otherwise it would be difficult or even impossible to bring both zones into contact during application.

Other Ingredients The base of a lipstick consists of waxes, to which oils, coloring pigments, biogenic active substances and treatment substances and optionally further odorants are added.

Fats and Waxes

Typical examples of fats are glycerides, i.e. solid or liquid vegetable or animal products, which essentially consist of mixed glycerol esters of higher fatty acids; waxes that may be considered include, among others: natural waxes, e.g. candelilla wax, carnauba wax, Japan wax, esparto wax, cork wax, guaruma wax, rice germ oil wax, sugar cane wax, ouricury wax, montan wax, beeswax, shellac wax, spermaceti, lanolin (wool wax), preen oil, ceresin, ozokerite (earth wax), petrolatum, paraffin waxes, microwaxes; chemically modified waxes (hard waxes), e.g. montan ester waxes, Sasol waxes, hydrogenated jojoba waxes and synthetic waxes, e.g. polyalkylene waxes and polyethylene glycol waxes. Besides the fats, fat-like substances, such as lecithins and phospholipids, may also come into consideration as additives. The designation "lecithins" is understood by a person skilled in the art as including those glycero-phospholipids that form from fatty acids, glycerol, phosphoric acid and choline by esterification. Therefore in industry, lecithins are often phosphatidylcholines (PC). As examples of natural lecithins cephalins may be mentioned, which are also called phosphatide acids, and are derivatives of 1,2-diacyl-sn-glycerol-3-phosphoric acids. On the other hand, phospholipids are usually understood to mean mono- and preferably diesters of phosphoric acid with glycerol (glycerol phosphates), which are generally classed among the fats. In addition, sphingosines or sphingolipids may be considered.

Lanolin, beeswax, ozokerite wax and carnauba wax and any mixtures thereof are especially preferred.

Oils

As oils, the following may be considered, for example Guerbet alcohols based on fatty alcohols with 6 to 18, preferably 8 to 10 carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$ fatty acids with branched alcohols, especially 2-ethylhexanol, esters of $C_{18}$-$C_{38}$ alkylhydroxy carboxylic acids with linear or branched $C_6$-$C_{22}$ fatty alcohols, especially dioctyl malates, esters of linear and/or branched fatty acids with polyhydric alcohols (e.g. propylene glycol, dimer diol or trimer triol) and/or Guerbet alcohols, triglycerides based on $C_6$-$C_{10}$ fatty acids, liquid mono-/di-/triglyceride mixtures based on $C_6$-$C_{18}$ fatty acids, esters of $C_6$-$C_{22}$ fatty alcohols and/or Guerbet alcohols with aromatic carboxylic acids, especially benzoic acid, esters of $C_2$-$C_{12}$ dicarboxylic acids with linear or branched alcohols with 1 to 22 carbon atoms or polyols with 2 to 10 carbon atoms and 2 to 6 hydroxyl groups, vegetable oils, branched primary alcohols, substituted cyclohexanes, linear and branched $C_6$-$C_{22}$ fatty alcohol carbonates, e.g. dicaprylyl carbonates (Cetiol® CC), Guerbet carbonates based on fatty alcohols with 6 to 18, preferably 8 to 10 carbon atoms, esters of benzoic acid with linear and/or branched $C_6$-$C_{22}$ alcohols (e.g. Finsolv® TN), linear or branched, symmetric or asymmetric dialkyl ethers with 6 to 22 carbon atoms per alkyl group, e.g. dicaprylyl ether (Cetiol® OE), ring-opening products of epoxidized fatty acid esters with polyols, silicone oils (cyclomethicones, silicon methicone types etc.) and/or aliphatic or naphthenic hydrocarbons, e.g. squalane, squalene or dialkylcyclohexanes may come into consideration.

Overfatting Agents and Stabilizers

As overfatting agents, it is possible to use substances such as for example lanolin and lecithin and polyethoxylated or acylated lanolin and lecithin derivatives, polyol fatty acid esters, monoglycerides and fatty acid alkanolamides, wherein the latter serve simultaneously as foam stabilizers.

Metal salts of fatty acids, e.g. magnesium, aluminum and/or zinc stearate or ricinoleate may be used as stabilizers.

Polymers

Suitable cationic polymers are for example cationic cellulose derivatives, e.g. a quaternized hydroxyethylcellulose, which is available from Amerchol under the designation Polymer JR 400®, cationic starch, copolymers of dialylammonium salts and acrylamides, quaternized vinylpyrrolidone/vinylimidazole polymers, e.g. Luviquat® (BASF), condensation products of polyglycols and amines, quaternized collagen polypeptides, for example lauryldimonium Hydroxypropyl Hydrolyzed Collagen (Lamequat®L/Gridnau), quaternized wheat polypeptides, polyethylenimines, cationic silicone polymers, e.g. amodimethicones, copolymers of adipic acid and dimethyl-aminohydroxypropyldiethylene triamine (Cartaretine®/Sandoz), copolymers of acrylic acid with dimethyl-diallyl ammonium chloride (Merquat® 550/Chemviron), polyamino polyamides and cross-linked water-soluble polymers thereof, cationic chitin derivatives such as for example quaternized chitosan, optionally microcrystalline, condensation products from dihalogen alkylenes, e.g. dibromobutane with bisdialkylamines, e.g. bis-dimethylamino-1,3-propane, cationic guar gum, e.g. Jaguar® CBS, Jaguar® C-17, Jaguar® C-16 from the company Celanese, quaternized ammonium salt polymers, e.g. Mirapol® A-15, Mirapol® AD-1, Mirapol® AZ-1 from the company Miranol.

As anionic, zwitterionic, amphoteric and nonionic polymers, consideration may be given for example to vinyl acetate/crotonic acid copolymers, vinylpyrrolidone/vinylacrylate copolymers, vinyl acetate/butyl maleate/isobornyl acrylate copolymers, methylvinyl ether/maleic acid anhydride copolymers and esters thereof, uncrosslinked and polyol-crosslinked polyacrylic acids, acrylamidopropyltrimethylammonium chloride/acrylate copolymers, octylacrylamide/methyl-methacrylate/tert-butylaminoethylmethacrylate/2-hydroxypropylmethacrylate copolymers, polyvinylpyrrolidone, vinylpyrrolidone/vinyl acetate copolymers, vinylpyrrolidone/dimethylaminoethyl-methacrylate/vinylcaprolactam terpolymers and if applicable derivatized cellulose ethers and silicones.

Silicone Compounds

Suitable silicone compounds are for example dimethylpolysiloxanes, methylphenylpolysiloxanes, cyclic silicones and amino-, fatty acid-, alcohol-, polyether-, epoxy-, fluoro-, glycoside- and/or alkyl-modified silicone compounds, which may be both liquid and resinous at room temperature. Others that are suitable are simethicones, which are mixtures of dimethicones with an average chain length of 200 to 300 dimethylsiloxane units and hydrogenated silicates.

UV Light Protection Factors

UV light protection factors are to be understood as for example organic substances that are liquid or crystalline at room temperature (light protection filters), which are capable of absorbing ultraviolet rays and re-emitting the absorbed energy in the form of longer-wave radiation, e.g. heat. Usually the UV light protection factors are present in amounts from 0.1 to 5 and preferably 0.2 to 1 wt %. UVB filters may be oil-soluble or water-soluble. As oil-soluble substances, mention can be made, for example, of:

3-Benzylidene camphor or 3-benzylidene norcamphor and derivatives thereof, e.g. 3-(4-methylbenzylidene) camphor described;

4-Aminobenzoic acid derivatives, preferably 4-(dimethylamino)benzoic acid-2-ethylhexyl ester, 4-(dimethylamino)benzoic acid-2-octyl ester and 4-(dimethylamino) benzoic acid amyl ester;

Esters of cinnamic acid, preferably 4-methoxycinnamic acid-2-ethylhexyl ester, 4-methoxycinnamic acid propyl ester, 4-methoxycinnamic acid isoamyl ester, 2-cyano-3, 3-phenylcinnamic acid-2-ethylhexyl ester (Octocrylenes);

Esters of salicylic acid, preferably salicylic acid-2-ethylhexyl ester, salicylic acid-4-isopropylbenzyl ester, salicylic acid homomenthyl ester;

Derivatives of benzophenone, preferably 2-hydroxy-4-methoxybenzophenone, 2-hydroxy-4-methoxy-4'-methylbenzophenone, 2,2'-dihydroxy-4-methoxybenzophenone;

Esters of benzalmalonic acid, preferably 4-methoxybenzmalonic acid di-2-ethylhexyl ester;

Triazine derivatives, e.g. 2,4,6-trianilino-(p-carbo-2'-ethyl-1'-hexyloxy)-1,3,5-triazine and Octyl Triazone or Dioctyl Butamido Triazone (Uvasorb® HEB);

Propane-1,3-diones, e.g. 1-(4-tert-butylphenyl)-3-(4'-methoxyphenyl)propane-1,3-dione;

Ketotricyclo(5.2.1.0)decane derivatives.

The following may come into consideration as water-soluble substances:

2-Phenylbenzimidazole-5-sulfonic acid and alkali-metal, alkaline-earth, ammonium, alkylammonium, alkanolammonium and glucammonium salts thereof;

1H-Benzimidazole-4,6-disulfonic acid, 2,2'-(1,4-phenylene) bis-, disodium salt (Neo Heliopan® AP)

Sulfonic acid derivatives of benzophenones, preferably 2-hydroxy-4-methoxybenzophenone-5-sulfonic acid and salts thereof;

Sulfonic acid derivatives of 3-benzylidene camphors, e.g. 4-(2-oxo-3-bornylidene)methyl)benzenesulfonic acid and 2-methyl-5-(2-oxo-3-bornylidene)sulfonic acid and salts thereof.

Typical UV-A filters are in particular derivatives of benzoyl methane, such as for example 1-(4'-tert-butylphenyl)-3-(4'-methoxyphenyl)propane-1,3-dione, 4-tert.-butyl-4'-methoxydibenzoyl methane (Parsol® 1789), 2-(4-diethylamino-2-hydroxybenzoyl)benzoic acid hexyl ester (Uvinul® A Plus), 1-phenyl-3-(4'-isopropylphenyl)-propane-1,3-dione and enamine compounds. The UV-A and UV-B filters may of course also be used in mixtures.

Especially favorable combinations consist of the derivatives of benzoyl methane, e.g. 4-tert.-butyl-4'-methoxydibenzoyl methane (Parsol® 1789) and 2-cyano-3,3-phenylcinnamic acid-2-ethyl-hexyl ester (Octocrylenes) in combination with esters of cinnamic acid, preferably 4-methoxy cinnamic acid-2-ethylhexyl ester and/or 4-methoxy cinnamic acid propyl ester and/or 4-methoxy cinnamic acid isoamyl ester. Advantageously, said combinations are combined with water-soluble filters, e.g. 2-phenylbenzimidazole-5-sulfonic acid and alkali-metal, alkaline-earth, ammonium, alkylammonium, alkanolammonium and glucammonium salts thereof.

Besides the aforementioned soluble substances, insoluble light protective pigments, namely finely dispersed metal oxides or salts may also be considered for this purpose. Examples of suitable metal oxides are in particular zinc oxide and titanium dioxide and in addition oxides of iron, zirconium, silicon, manganese, aluminum and cerium and mixtures thereof. Silicates (talc), barium sulfate or zinc stearate may be used as salts. The oxides and salts are used in the form of pigments for skin-care and skin-protection emulsions and decorative cosmetics. The particles should then have an average diameter of less than 100 nm, preferably between 5 and 50 nm and especially between 15 and 30 nm. They may have a spherical shape, but it is also possible to use particles that have an ellipsoidal shape or a shape differing from spherical in some other way. The pigments may also be surface-treated, i.e. hydrophilized or hydrophobized. Typical examples are coated titanium dioxides, e.g. titanium dioxide T 805 (Degussa) or Eusolex® T2000, Eusolex® T, Eusolex® T-ECO, Eusolex® T-S, Eusolex® T-Aqua, Eusolex® T-45D (all from Merck), Uvinul $TiO_2$ (BASF). As hydrophobic coating agents, mainly silicones and especially trialkoxyoctylsilanes or simethicones may be considered. So-called micro- or nanopigments are preferably used in sunscreen agents. Preferably micronized zinc oxide, e.g. Z-COTE® or Z-COTE HP1®, is used.

Humectants

Humectants serve for further optimization of the sensory properties of the composition and for moisture control of the skin. At the same time, the low-temperature stability of the preparations according to the invention, especially in the case of emulsions, is increased. Humectants are usually contained in an amount from 0.1 to 15 wt %, preferably 1 to 10 wt %, and especially 5 to 10 wt %.

Among others, amino acids, pyrrolidone carboxylic acid, lactic acid and salts thereof, lactitol, urea and urea derivatives, uric acid, glucosamine, creatinine, cleavage products of collagen, chitosan or chitosan salts/derivatives, and especially polyols and polyol derivatives (e.g. glycerol, diglycerol, triglycerol, ethylene glycol, propylene glycol, butylene glycol, erythritol, 1,2,6-hexanetriol, polyethylene glycols such as PEG-4, PEG-6, PEG-7, PEG-8, PEG-9, PEG-10, PEG-12, PEG-14, PEG-16, PEG-18, PEG-20), sugars and sugar derivatives (among others fructose, glucose, maltose, maltitol, mannitol, inositol, sorbitol, sorbitylsilanediol, sucrose, trehalose, xylose, xylitol, glucuronic acid and salts thereof), ethoxylated sorbitol (Sorbeth-6, Sorbeth-20, Sorbeth-30, Sorbeth-40), honey and hardened honey, hardened starch hydrolyzates and mixtures of hardened wheat protein and PEG-20 acetate copolymer are suitable according to the invention. Glycerol, diglycerol, triglycerol and butylene glycol are suitable and preferable as humectants according to the invention.

Biogenic Active Substances and Antioxidants

For example tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramide, pseudoceramides, essential oils, plant extracts, e.g. Prunus extract, bambara groundnut extract and vitamin complexes are to be understood as biogenic active substances.

Antioxidants interrupt the photochemical reaction chain that is triggered when UV radiation penetrates into the skin. Typical examples of these are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthioracil and other thiols (e.g. thioredoxin, glutathione, cysteine, cystine, cystamine and glycosyl-, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximine, homocysteine sulfoximine, buthionine sulfones, penta-, hexa-, heptathionine sulfoximine) in very small compatible dosages (e.g. pmol to µmol/kg), furthermore (metal) chelators (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg-ascorbyl phosphate, ascorbyl acetate), tocopherols and derivatives (e.g. vitamin-E acetate), vitamin A and derivatives (vitamin-A palmitate) and coniferyl benzoate of benzoic resin, rutinic acid and derivatives thereof, α-glycosylrutin, ferulic acid, furfurylidene glucitol, carnosine, butylhydroxytoluene, butylhydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$), selenium and derivatives thereof (e.g. selenium methionine), stilbenes and derivatives thereof (e.g. stilbene oxide, trans-stilbene oxide) and the derivatives suitable according to the invention (salts, esters, ethers, sugars, nucleotides, nucleosides, peptides and lipids) of the aforementioned active substances.

Colorants

The colorants that may be used are the substances that are suitable and permitted for cosmetic purposes, as given for example in the publication "Kosmetische Färbemittel" ("Cosmetic coloring agents") of the Coloring Matter Commission of the Deutsche Forschungsgemeinschaft (German Research Association), Verlag Chemie, Weinheim, 1984, p.81-106. Examples are Cochineal Red A (C.I. 16255), and Madder Lake (C.I. 58000). Coloring pigments or colored lakes are preferably used, for example mica pigments.

Additional Perfume Oils and Flavorings

As additional perfume oils, mention may be made of mixtures of natural and synthetic fragrances. Natural fragrances are flower extracts (lily, lavender, rose, jasmine, neroli, ylang-ylang), stems and leaves (geranium, patchouli, petitgrain), fruits (anise, coriander, caraway, juniper), peel (bergamot, lemon, orange), spices (mace, angelica, celery, cardamon, costus, iris, calamus), wood (pinewood, sandalwood, guaiac, cedar wood, rosewood), herbs and grasses (tarragon, lemongrass, sage, thyme), needles and branches (spruce, fir, pine, mountain pine), resins and balsams (galbanum, elemi, benzoin, myrrh, olibanum, opopanax). Animal raw materials may also be considered, for example civet and castoreum. Typical synthetic fragrance compounds are products of the type of esters, ethers, aldehydes, ketones, alcohols and hydrocarbons. Fragrance compounds of the ester type are e.g. benzyl acetate, phenoxyethyl isobutyrate, p-tert.-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include for example benzylethyl ether, the aldehydes include e.g. the linear alkanals with 8 to 18 carbon atoms, citral, citronellal, citronellyl oxyacetaldehyde, cyclamen aldehyde, hydroxycitronellal, lilial and bourgeonal, the ketones include e.g. the ionones, α-isomethylionone and methylcedryl ketone, the alcohols include anethole, citronellol, eugenol, isoeugenol, geraniol, linalool, phenylethyl alcohol and terpineol, the hydrocarbons include mainly the terpenes and balsams. Preferably, however, mixtures of various fragrances are used, which together produce an attractive perfume note. Also lower-volatility ethereal oils, which are mostly used as flavor components, are suitable as perfume oils, e.g. sage oil, chamomile oil, clove oil, melissa oil, mint oil, cinnamon leaf oil, linden blossom oil, juniper berry oil, vetiver oil, olibanum oil, galbanum oil, labolanum oil and lavandin oil. Bergamot oil, dihydromyrcen oil, lilial, lyral, citronellol, phenylethyl alcohol, α-hexylcinnamic aldehyde, geraniol, benzyl acetone, cyclamen aldehyde, linalool, Boisambrene Forte, Ambroxan, indole, hediones, sandalice, lemon oil, mandarin oil, orange oil, allylamyl glycolate, cyclovertal, lavandin oil, clary sage oil, β-damascone, geranium oil Bourbon, cyclohexyl salicylate, Vertofix Coeur, Iso-E-Super, Fixolide NP, Evernyl, iraldeine gamma, phenylacetic acid, geranyl acetate, benzyl acetate, rose oxide, Romilllat, irotyl and Floramate alone or in mixtures, are preferably used.

As flavorings, for example peppermint oil, spearmint oil, anise oil, star anise oil, caraway oil, eucalyptus oil, fennel oil, lemon oil, oil of wintergreen, clove oil, menthol and the like may also be considered.

Oral Preparations

The invention further relates to oral preparations containing
(a) a carrier with at least one fruit flavoring with a red taste impression and
(b) a carrier with at least one fruit flavoring with a green taste impression,
wherein the two carriers (a) and (b) are spatially separated from one another, but are adjacent.

Preferably the preparations are toothpastes or tooth creams or chewing gums.

Toothpastes or Tooth Creams

Toothpastes or tooth creams are essentially pasty preparations made of water, consistency regulators, humectants, abrasive or scouring substances, sweeteners, aromatic substances, deodorizing active substances and active substances against mouth and tooth diseases. All the usual scouring materials, e.g. chalk, dicalcium phosphate, insoluble sodium metaphosphate, aluminum silicates, calcium pyrophosphate, finely-divided synthetic resins, silicic acids, aluminum oxide and aluminum oxide trihydrate may be used in the toothpastes according to the invention.

Preferred suitable scouring materials for the toothpastes according to the invention are in particular finely-divided xerogel silicic acids, hydrogel silicic acids, precipitated silicic acids, aluminum oxide trihydrate and finely-divided alpha-aluminum oxide or mixtures of these scouring materials in amounts from 15 to 40 wt % of the toothpaste.

For example glycerol, sorbitol, xylitol, propylene glycols, polyethylene glycols, especially those with average molecular weights of 200-800, may be used as humectants. For example natural and/or synthetic water-soluble polymers such as carrageenates, tragacanth, starch and starch ethers, cellulose ethers, e.g. carboxymethylcellulose (Na salt), hydroxyethylcellulose, methylhydroxypropylcellulose, guar, acacia gum, agar, xanthan gum, carob flour, pectins, water-soluble carboxyvinyl polymers (e.g. Carbopol types), polyvinyl alcohol, polyvinylpyrrolidone, polyethylene glycol, especially those with molecular weights from 1500 to 1000000, are used as consistency regulators (or binders).

Other substances that are suitable for viscosity control are for example layer silicates, e.g. montmorillonite clays, colloidal thickening silica e.g. aerogel silica or pyrogenic silicas. A carrier particularly suitable for the flavorings contains e.g.
20 to 35 wt % water
20 to 35 wt % sorbitol
5 to 15 wt % glycerol
2 to 10 wt % polyethylene glycol (average molecular weight 200-800)
0.1 to 0.5 wt % carboxymethylcellulose
1 to 3 wt % thickening silica and
14 to 40 wt % abrasive and scouring materials, and
0.1 to 0.5 wt % flavorings.

Other usual toothpaste additives are
preservatives and antimicrobial agents, e.g. p-hydroxybenzoic acid methyl, ethyl or propyl esters, sodium sorbate, sodium benzoate, bromochlorophene, phenyl salicylates, thymol etc.
anti-tartar agents, e.g. organophosphonates such as the sodium salts of 1-hydroxyethane-1,1-diphosphonic acid, azacycloheptane 1-phosphonopropane-1,2,3-tricarboxylic acid and other phosphonic acids,
caries-inhibiting substances, e.g. sodium fluoride, sodium monofluorophosphate, tin fluoride
sweeteners, e.g. saccharin sodium, sodium cyclamate, sucrose, lactose, maltose, fructose,
flavorings, e.g. peppermint oil, spearmint oil, eucalyptus oil, anise oil, fennel oil, caraway oil, menthyl acetate, cinnamaldehyde, anethole, vanillin, thymol and mixtures of these and other natural and synthetic flavorings,
pigments, e.g. titanium dioxide
dyes
buffer substances, e.g. primary, secondary or tertiary alkali phosphates or citric acid/sodium citrate,
wound-healing and anti-inflammatory agents, e.g. allantoin, urea and azulene, chamomile active substances, acetylsalicylic acid derivatives.

Toothpastes are as a rule filled in the containers by extrusion, double-strand extrusion being recommended, because then a different flavoring can be added to each of the two strands.

Chewing Gums

Chewing gums typically contain a water-insoluble component and a water-soluble component, wherein the flavorings, at least one of which should be encapsulated, are preferably in the water-soluble phase.

The water-insoluble base, which is also called "gum base", usually comprises natural or synthetic elastomers, resins, fats and oils, plasticizers, fillers, colorants and optionally waxes. The proportion of the base in the total composition is usually 5 to 95, preferably 10 to 50 and especially 20 to 35 wt %. In a typical embodiment of the invention, the base consists of 20 to 60 wt % synthetic elastomers, 0 to 30 wt % natural elastomers, 5 to 55 wt % plasticizers, 4 to 35 wt % fillers and minor amounts of additives such as colorants, antioxidants and the like, with the proviso that they are water-soluble, at least in small amounts.

Suitable synthetic elastomers are for example polyisobutylenes with average molecular weights (according to GPC) from 10000 to 100000 and preferably 50000 to 80000, isobutylene-isoprene copolymers ("butyl elastomers"), styrene-butadiene copolymers (styrene:butadiene ratio e.g. 1:3 to 3:1), polyvinyl acetates with average molecular weights (according to GPC) from 2000 to 90000 and preferably 10000 to 65000, polyisoprenes, polyethylene, vinyl acetate-vinyl laurate copolymers and mixtures thereof. Examples of suitable natural elastomers are rubber such as smoked or liquid latex or guayule and natural gum substances such as jelutong, lechi caspi, perillo, sorva, massaranduba balata, massaranduba chocolate, nispero, rosindinba, chicle, gutta hang kang and mixtures thereof. Selection of the synthetic and natural elastomers and the mixing ratios for them are based essentially on whether or not the chewing gum is intended to produce bubbles ("bubble gums"). Preferably, elastomer mixtures are used that contain jelutong, chicle, sorva and massaranduba.

In most cases the elastomers have proved in processing to be too hard or inadequately deformable, so that it has proved advantageous to use special softeners with them, which of course in particular must also all meet the requirements for authorization as food additives. In this respect, mainly esters of resin acids may be considered, for example esters of lower aliphatic alcohols or polyols with fully or partially hardened, monomeric or oligomeric resin acids. In particular, the methyl, glycerol, or pentaerythritol esters and mixtures thereof are used for this purpose. Alternatively terpene resins, which may be derived from alpha-pinene, beta-pinene, delta-limonene and/or mixtures thereof, may also be considered.

Fillers or texturing agents include magnesium or calcium carbonate, ground pumice stone, silicates, especially magnesium or aluminum silicates, clays, aluminum oxides, talc, titanium dioxide, mono-, di- and tricalcium phosphate and cellulose polymers.

Suitable emulsifiers are tallow, hardened tallow, hardened or partially hardened vegetable oils, cocoa butter, partial glycerides, lecithin, triacetin and saturated or unsaturated fatty acids with 6 to 22 and preferably 12 to 18 carbon atoms and mixtures thereof.

As colorants and whitening agents, for example the FD and C types permitted for the coloring of foodstuffs, plant and fruit extracts and titanium dioxide may be considered.

The base mass may contain waxes or may be wax-free; examples of wax-free compositions are given inter alia in the patent document U.S. Pat. No. 5,286,500, the contents of which are referred to expressly hereby.

In addition to the water-insoluble gum base, chewing gum preparations regularly contain a water-soluble fraction, which consists for example of softeners, sweeteners, fillers, flavorings, flavor enhancers, emulsifiers, colorants, acidifying agents, antioxidants and the like, here with the proviso that the constituents possess an at least sufficient water solubility. Depending on the water solubility of the particular representatives, individual constituents may accordingly appertain both to the water-insoluble and to the water-soluble phase. However, it is also possible to use combinations of for example a water-soluble and a water-insoluble emulsifier, wherein the individual representatives are then in different phases. Usually the water-insoluble fraction makes up 5 to 95 and preferably 20 to 80 wt % of the preparation.

Water-soluble softeners or plasticizers are added to the chewing gum in order to improve the chewability and the chewing feel, and are present in the mixtures typically in amounts from 0.5 to 15 wt %. Typical examples are glycerol, lecithin and aqueous solutions of sorbitol, hardened starch hydrolyzates or corn sirup.

As sweeteners, both sugar-containing and sugar-free compounds may be considered, which are used in amounts from 5 to 95, preferably 20 to 80 and especially 30 to 60 wt % relative to the chewing gum composition. Typical saccharide sweeteners are sucrose, dextrose, maltose, dextrin, dried invert sugar, fructose, levulose, galactose, corn sirup and mixtures thereof. As sugar substitutes, sorbitol, mannitol, xylitol, hardened starch hydrolyzates, maltitol and mixtures thereof may be considered. Moreover, as additives, so-called HIASs ("High Intensity Artificial Sweeteners") may also be considered, such as for example Sucralose, aspartame, acesulfame salts, Alitam, saccharin and saccharin salts, cyclamic acid and salts thereof, glycyrrhizins, dihydrochalcone, thaumatin, monellin and the like, alone or mixed. The hydrophobic HIASs, which are the subject matter of international patent application WO 2002 091849 A1 (Wrigleys) and stevia extracts and the active constituents thereof, especially Rebaudioside A, are also especially effective. The amount of these substances to be used depends primarily on their effectiveness and is typically in the range from 0.02 to 8 wt %.

Fillers such as for example polydextrose, Raftilose, Rafitilin, fructo-oligosaccharides (NutraFlora), Palatinose oligosaccharides, guar gum hydrolyzates (Sun Fiber) and dextrins are suitable in particular for the production of low-calorie chewing gum.

Usually the total proportion of all aromatic substances is 0.1 to 15 and preferably 0.2 to 5 wt % relative to the chewing gum composition. Chewing gums may further contain auxiliaries and additives, which are suitable for example for dental hygiene, especially for controlling plaque and gingivitis, e.g. chlorhexidine, CPC or triclosan. In addition, pH regulators (e.g. buffers or urea), active substances against caries (e.g. phosphates or fluorides), biogenic active substances (antibodies, enzymes, caffeine, plant extracts) may be present, provided these substances are permitted for foodstuffs.

Foodstuffs

The invention further relates to foodstuffs containing
(a) a carrier with at least one fruit flavoring with a red taste impression and
(b) a carrier with at least one fruit flavoring with a green taste impression,
wherein the two carriers (a) and (b) are spatially separated from one another, but are adjacent.

The foodstuffs may basically be baked products, for example bread, dry biscuits, cakes, other baked goods, confectionery (for example chocolates, chocolate bar products, other bar products, fruit gum, hard and soft caramels, chewing gum), alcoholic or nonalcoholic beverages (for example coffee, tea, iced tea, wine, wine-containing beverages, beer, beer-containing beverages, liqueurs, schnapps, brandies, (carbonated) fruit-containing lemonades, (carbonated) isotonic beverages, (carbonated) soft drinks, nectars, spritzers, fruit and vegetable juices, fruit or vegetable juice preparations, instant drinks (for example instant cocoa drinks, instant tea drinks, instant coffee drinks, instant fruit drinks), meat products (for example ham, fresh sausage or raw sausage preparations, spiced or marinated fresh or salted meat products), eggs or egg products (dried egg, egg white, egg yolk), cereal products (for example breakfast cereals, muesli bars, precooked finished rice products), milk products (for example milk drinks, butter milk drinks, milk-based ice cream, yoghurt, kefir, fresh cheese, soft cheese, hard cheese, dried milk powder, whey, whey beverages, butter, buttermilk, partially or fully hydrolyzed lactoprotein-containing products), products from soy protein or other soybean fractions (for example soybean milk and products prepared therefrom, fruit beverages with soy protein, soy lecithin-containing preparations, fermented products such as tofu or tempeh or products prepared therefrom), products from other vegetable protein sources, for example oat protein beverages, fruit preparations (for example jams, fruit ice cream, fruit sauces, fruit fillings), vegetable preparations (for example ketchup, sauces, dried vegetables, frozen vegetables, precooked vegetables, preserved vegetables), nibbles (for example roasted or fried potato chips or potato dough products, maize- or peanut-based extrudates), fat-based and oil-based products or emulsions thereof (for example mayonnaise, remoulade, dressings), other ready-meals and soups (for example dried soups, instant soups, precooked soups), spices, spice mixtures and especially seasonings, which for example find application in the domain of snacks. In these cases it is recommended for at least one of the two flavorings to be encapsulated.

Preferably the foodstuffs are fruit gums, pastilles or hard caramels.

INDUSTRIAL APPLICABILITY

The invention further relates to the use of mixtures of
(a) at least one fruit flavoring with a red taste impression and
(b) at least one fruit flavoring with a green taste impression
for producing a fruit flavoring with a yellow taste impression. The fruit flavorings with a red taste impression and the fruit flavorings with a green taste impression are preferably brought into contact or mixed in a weight ratio from about 25:75 to about 75:25. A weight ratio from about 40:60 to about 60:40 and especially about 50:50 is especially preferred.

In particular, the invention relates to the use of the mixtures for making the aforementioned cosmetic or oral preparations and foodstuffs.

EXAMPLES

Example 1

Production of a Pear Flavoring
A red strawberry flavoring and a green apple flavoring were mixed in the weight ratio 1:1. The compositions of the two flavorings are shown in Table 1.

TABLE 1

Strawberry and apple flavoring

| Component | Strawberry flavoring | Apple flavoring |
|---|---|---|
| Isoamyl acetate | — | 0.200 |
| Ethyl acetate | — | 1.500 |
| Aldehyde C6 | — | 0.500 |

TABLE 1-continued

Strawberry and apple flavoring

| Component | Strawberry flavoring | Apple flavoring |
|---|---|---|
| Hexenol trans-2 | — | 3.00 |
| Hexenal trans-2 | — | 6.00 |
| Alcohol C6 | — | 3.00 |
| n-Butanol | — | 2.00 |
| Diacetyl | 0.030 | — |
| Ethyl isovalerate | 0.030 | — |
| Methylbutyric acid-2 | 0.060 | — |
| Ethyl isobutyrate | 0.120 | — |
| Ethyl caproate | 0.120 | — |
| Ethyl pelargonate | 0.120 | — |
| Methylmethyl butyrate | 0.480 | — |
| Decalactone gamma | 1.00 | — |
| Hexenol cis-3 | 1.300 | — |
| Ethylmethyl butyrate-2 | 2.00 | — |
| Aldehyde C14 | 3.100 | — |
| Ethyl maltol | 12.000 | — |
| Propylene glycol-1,2 | To 100 ||

Example 2

Production of a Peach Flavoring

A red raspberry flavoring and a green apple flavoring were mixed in the weight ratio 1:1. The compositions of the two flavorings are shown in Table 2.

TABLE 2

Raspberry and apple flavoring

| Component | Strawberry flavoring | Apple flavoring |
|---|---|---|
| Isoamyl acetate | — | 0.200 |
| Ethyl acetate | — | 1.500 |
| Aldehyde C6 | — | 0.500 |
| Hexenol trans-2 | — | 3.00 |
| Hexenal trans-2 | — | 6.00 |
| Alcohol C6 | — | 3.00 |
| n-Butanol | — | 2.00 |
| Geraniol | 0.050 | — |
| Maltol | 0.100 | — |
| Hexenol cis-3 | 0.100 | — |
| Damascenone | 0.300 | — |
| Acetic acid | 0.500 | — |
| Ionone beta | 0.800 | — |
| Ethyl butyrate | 1.000 | — |
| Phenylethyl butyrate | 1.000 | — |
| Isoamyl propionate | 1.800 | — |
| Isoamyl butyrate | 3.500 | — |
| Isoamyl acetate | 5.000 | — |
| Frambinone | 5.000 | — |
| Propylene glycol-1,2 | To 100 ||

Formulation Examples

The following Table 3 gives formulation examples for lipstick recipes. The designation "Flavorings" is to be understood as meaning that the corresponding recipe is produced once with a red and once with a green flavoring and both recipes are then made separately from one another into the lipstick, wherein then one side of the stick contains the red flavoring and the other contains the green flavoring.

TABLE 3

Lipstick formulations

| Components | 1 | 2 | 3 | 4 | 5 | 6 | 7 | 8 | 9 | 10 |
|---|---|---|---|---|---|---|---|---|---|---|
| Cera Microcristallina | 16 | 16 | 14 | 14 | 14 | 16 | 18 | 14 | 14 | 14 |
| Beeswax | 4 | — | 3 | 3 | 2 | 4 | 2 | 1 | 3 | 4 |
| Carnauba Wax | — | 4 | 3 | 3 | 4 | — | — | 5 | 3 | 2 |
| Cetearyl Alcohol | 2 | 1 | 2 | 2 | 2 | 1 | 2 | 2 | 2 | 1 |
| Cetyl Palmitate | 4 | 4 | 3 | 2 | 5 | 5 | 6 | 4 | 3 | 4 |
| Octyldodecanol | 20 | 20 | 22 | 20 | 22 | 22 | 20 | 20 | 20 | 18 |
| Capric Caprylic Triglycerides | 20 | 15 | 20 | 20 | 20 | 20 | 20 | 15 | 15 | 15 |
| *Butyspermium Parkii* Butter | 1 | 1 | 1 | 1 | 1 | 1 | 1 | 1 | 1 | 1 |
| Myristyl Myristate | 2 | — | 2 | 4 | 4 | — | 4 | 2 | 2 | 4 |
| Cera Alba | 1 | 1 | 1 | 1 | 1 | — | 1 | 1 | — | 1 |
| *Ricinus Communis* Seed Oil | 8 | 10 | 10 | 10 | 8 | 12 | 12 | 12 | 12 | 12 |
| C20-40 Alkyl Stearate | 0.5 | 0.5 | 0.5 | 0.5 | 0.5 | 0.5 | 0.5 | 0.5 | 0.5 | 0.5 |
| *Vitis Viniferis* Seed Oil | 1 | 0.5 | 0.5 | 1 | 1 | — | — | 0.5 | 0.5 | — |
| Hyaluronic Acid | 0.1 | 0.1 | 0.1 | 0.1 | 0.1 | 0.1 | 0.1 | 0.1 | 0.1 | 0.1 |
| Hydrogenated Castor Oil | 1 | 1 | 1 | 1 | 1 | 1 | 1 | 1 | 1 | 1 |
| Polyglyceryl-3 Diisostearate | 2 | 2 | 2 | 2 | 2 | 2 | 2 | 2 | 2 | 2 |
| Flavoring | 0.1 | 0.1 | 0.1 | 0.1 | 0.1 | 0.1 | 0.1 | 0.1 | 0.1 | 0.1 |
| Glycerol | 10 | 10 | 12 | 10 | 10 | 12 | 9 | 13 | 12 | 12 |
| Phenoxyethanol | 0.5 | 0.5 | 0.5 | — | — | — | — | 0.5 | 0.5 | 0.5 |
| Water | To 100 | | | | | | | | | |

The invention claimed is:

1. A decorative cosmetic which comprises a fruit flavoring with a yellow taste impression of a fruit selected from the group consisting of peach and pear, obtained by contacting or mixing
   (a) at least one fruit flavoring with a red taste impression of a fruit selected from the group consisting of strawberry and raspberry and
   (b) at least one fruit flavoring with a green taste impression of an apple.

2. The decorative cosmetic of claim 1, obtained by bringing into contact or mixing the fruit flavorings with a red taste impression and the fruit flavorings with a green taste impression of in the weight ratio from about 25:75 to about 75:25.

3. The cosmetic as claimed in claim 1, which is a lipstick.

4. The cosmetic as claimed in claim 3, wherein the lipstick is in the shape of a hemisphere.

5. A lipstick, containing
   (a) a carrier with at least one fruit flavoring with a red taste impression of a fruit selected from the group consisting of strawberry and raspberry and
   (b) a carrier with at least one fruit flavoring with a green taste impression of an apple
   wherein the two carriers (a) and (b) are spatially separated from one another, but adjacent to each other on a tube of lipstick.

6. A lipstick which comprises a fruit flavoring with a yellow taste impression of a fruit that is selected from the group formed by peach and pear obtained by contacting or mixing
   (a) at least one fruit flavoring with a red taste impression of a fruit that is selected from the group formed by strawberry and raspberry and
   (b) at least one fruit flavoring with a green taste impression of an apple.

7. A method for producing a lipstick comprising a fruit flavoring with a yellow taste impression of a fruit selected from the group consisting of peach and pear comprising the following steps:
   (i) providing at least one fruit flavoring with a red taste impression of a fruit selected from the group consisting of strawberry and raspberry (component a),
   (ii) providing at least one fruit flavoring with a green taste impression of an apple (component b), and
   (iii) contacting or mixing the two components (a) and (b), and wherein the component (a) and component (b) are present in different flavor zones on a tube of lipstick, and mixing the component (a) and component (b) at a site of application by applying the lipstick to the site of application.

8. The method as claimed in claim 7, wherein the site of application is the human skin or mucosa of a user of lipstick.

* * * * *